US00PP31251P2

(12) United States Plant Patent
Hansen

(10) Patent No.: US PP31,251 P2
(45) Date of Patent: Dec. 17, 2019

(54) **X *MANGAVE* PLANT NAMED 'RACING STRIPES'**

(50) Latin Name: **x *Mangave* hybrid, *Manfreda* times *Agave***
Varietal Denomination: Racing Stripes

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,624

(22) Filed: Dec. 11, 2018

(51) Int. Cl.
*A01H 5/12* (2018.01)
*A01H 6/24* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Mangave* plant named 'Racing Stripes' characterized by a large mound of glaucous, deep-green with chartreuse-yellow leaf centers, semi-fleshy, longitudinally folded leaves. Leaves have large overall marginal spines with small, stiff, marginal teeth, and stiff terminal spines. Apical spines and marginal teeth start off yellowish and develop a cinnamon coloration. Foliage tends to be upright to outwardly in basal portion and then arches outwardly to slightly downwardly toward apex of older leaves. The new plant is suitable for the garden or as a potted plant in the garden or home.

1 Drawing Sheet

Botanical classification: x *Mangave* hybrid, *Manfreda* times *Agave*.

Variety denomination: 'Racing Stripes'.

STATEMENT REGARDING PRIOR DISCLOSURES UNDER 37 CFR 1.77(b)(6)

The first public disclosure of the claimed plant, in the form of a sale, was made by Walters Gardens, Inc. on Dec. 15, 2017 to Plant Delights Nursery, Inc. in a private sale. Plants for this sale were obtained from the inventor. No plants of x *Mangave* 'Racing Stripes' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Racing Stripes' that was hybridized by the inventor at a wholesale perennial nursery in Zeeland, Mich., USA as a cross between an unreleased, unnamed, proprietary *Manfreda maculosa* x *Agave gypsophylla* (not patented) given the breeder code H10-02-02 as the female or seed parent times *Agave lophantha* 'Bandaid' (not patented) as the male or pollen parent. The cross was performed on Feb. 6, 2014 and seeds were harvested and sown later in May of 2014. Through trials at the same nursery the plant was assigned the breeder code 14-15-1. The new plant has been successfully asexually propagated by sterile shoot-tip tissue culture and by offsets at the same nursery in Zeeland, Mich. The asexual tissue culture and offset propagation has been found to produce stable and identical plants that maintain all the unique characteristics of the original plant.

BRIEF SUMMARY OF THE INVENTION x *Mangave* 'Racing Stripes' differs from its parents as well as all other *Manfreda, Agave* and x *Mangave* known to the applicant. The female parent has a shorter and less upright habit with foliage that is wider, with mahogany spotting, more undulations and without the lighter green leaf midribs. The male parent is more upright in habit, with wider and more numerous leaves, foliage that is shorter and non-arching, medium green with more pronounced light green midrib, with larger and firmer marginal teeth of near-white color. The nearest comparison plants are 'Carnival' U.S. Plant patent application Ser. No. 16/501,028 and 'Pineapple Express' U.S. Plant Pat. No. 28,613. 'Carnival' has a lighter yellow variegation of more than just the midrib, the foliage is more flexible and arching, develop reddish-purple spots in high light exposure and has smaller, more flexible marginal teeth. 'Pineapple Express' is shorter and denser in habit and the leaves are more glaucous blue with intense purple spotting.

The new plant, 'Racing Stripes, is unique from all of the above cultivars and all *Agave*, x *Mangave* and *Manfreda* known to the inventor by the following combined traits:

1. Large mound of shiny, lanceolate to linear, internally fibrous leaves;
2. Leaf margins have large, firm, marginal teeth and apical spines starting off yellowish and developing a cinnamon color;
3. Leaf color is deep-green toward the margins with chartreuse-yellow top and bottom midrib;
4. Moderate growth rate;

5. Foliage is upright to outwardly toward stem and arches in outer one-third with age.

BRIEF DESCRIPTION OF THE DRAWING

The photograph of x *Mangave* 'Racing Stripes' demonstrates the overall appearance of the new plant including the unique traits as a four-year-old plant grown in a full-sun research area in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
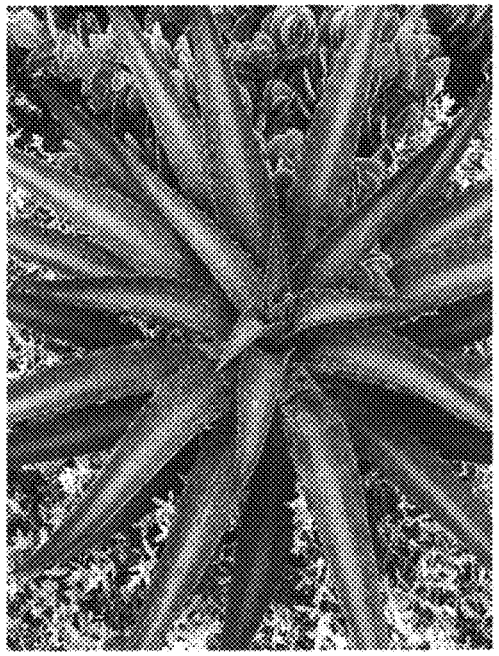
FIG. 1 shows a close-up side view of a plant with young and older foliage.
Figure 2:
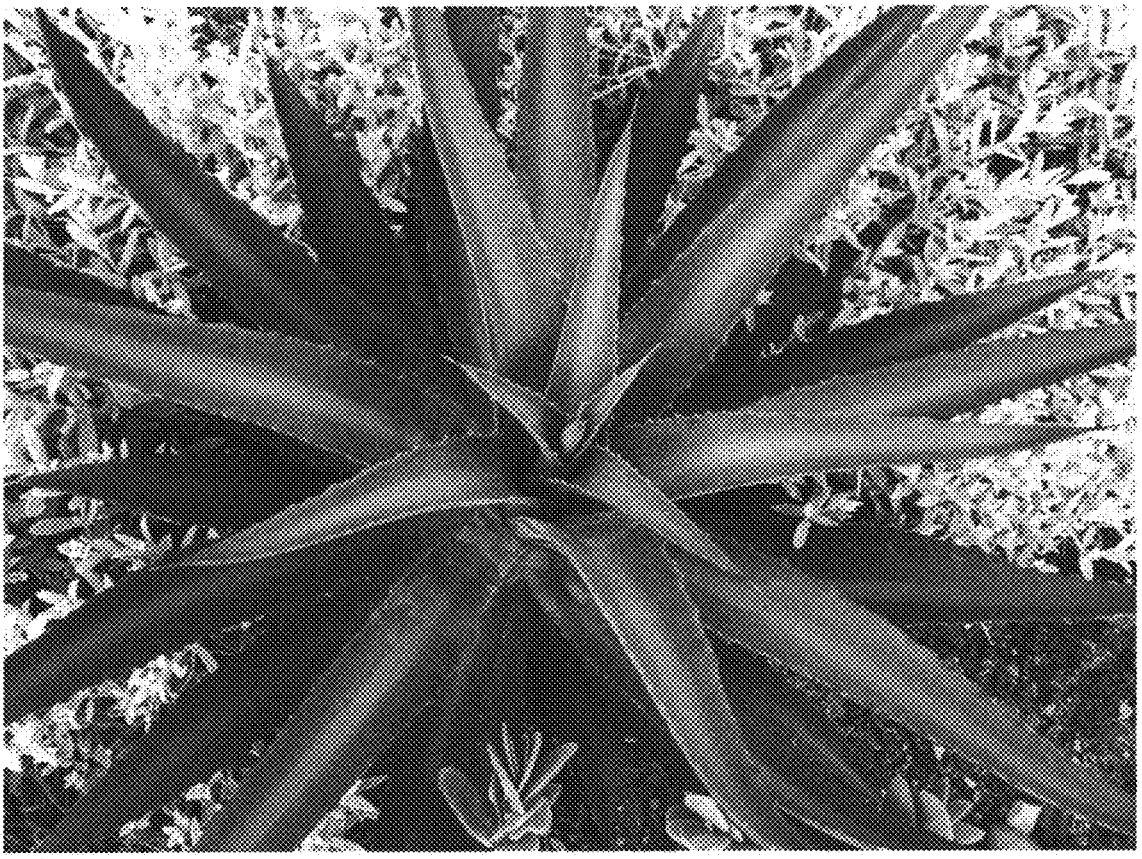
FIG. 2 shows a top view of the plant.

The following descriptions and color references are based on the 2015 edition of The Royal Horticultural Society Colour Chart except where common dictionary terms are used. The new plant, x *Mangave* 'Racing Stripes', has not been observed under all possible environments. The phenotype may vary slightly with different environmental conditions, such as temperature, light, fertility, moisture and maturity levels, but without any change in the genotype. The following observations and size descriptions are of a four-year-old plant in a full-sun research area in Zeeland, Mich. with supplemental water and fertilizer as needed.

Parentage: H10-02-02, an unnamed select form of *Manfreda maculosa* times *Agave gypsophylla* as female or seed patent and *Agave lophantha* 'Bandaid' as the male or pollen parent;

Propagation: By sterile shoot-tip tissue culture and offset;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 25 cm long;

Root color: Nearest RHS 158C;

Plant shape and habit: Succulent herbaceous perennial with basal rosettes of about 68 leaves radially emerging upwardly to outwardly from central stem then arching outwardly toward apical one-third with age, producing a radially-symmetrical, rounded mound;

Plant size: Foliage height about 56.0 cm tall from soil line to the top of the leaves and about 90.0 cm wide at the widest point about middle of the plant;

Foliage description: Lanceolate to linear; simple; sessile; bi-laterally symmetrical; apex narrowly acute with terminal spine; firm terminal spine to about 17.0 mm long and 3.5 mm wide at base; base truncate; mostly flat centers with flat margins; margins coarsely dentate with medium-sized firm teeth; glabrous abaxial and adaxial; glaucous abaxial and adaxial proximally toward stem becoming lustrous in distal two-thirds of leaves both abaxial and adaxial; highly fibrous;

Marginal teeth: Small, firm, sharp; about 4.0 mm long and 6.0 mm wide at base of tooth and about 5.7 mm apart in center on mature leaves;

Leaf size: To about 42.5 cm long, about 6.2 cm wide toward middle; center basal midrib about 20.0 mm thick; average about 44.0 cm long, 12.0 cm wide and 4.0 mm thick in longitudinal center;

Foliage fragrance: None observed;

Leaf number: About 68 per plant;

Leaf blade color:

*Adaxial* (*mature*).—Between nearest RHS 139A and RHS N189A at margins with midrib nearer RHS 147B than RHS 147A.

*Abaxial* (*mature*).—Nearest RHS 139A along marginal 3.0 mm, midrib nearest RHS 146D and region between midrib and margin nearest RHS 137B.

*Adaxial* (*young*).—Between RHS 141B and RHS 141C along margins, midrib nearest RHS 145A.

*Abaxial* (*young*).—Between RHS 141B and RHS 141C along margins, midrib nearest RHS 144B.

*Teeth*.—Blend between RHS 166A and RHS 178A.

*Terminal spine*.—Nearest RHS 166A.

Petiole: Leaves sessile;

Veins: Parallel; midrib about one-third the width of leaf; secondary veins not distinct abaxial or adaxial;

Flower description: Not yet observed;

Fruit and seed not observed;

Disease resistance: x *Mangave* 'Racing Stripes' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Racing Stripes' as herein described and illustrated.

* * * * *